May 11, 1954 H. R. CAMPBELL Plant Pat. 1,274
ROSE PLANT
Filed April 13, 1953
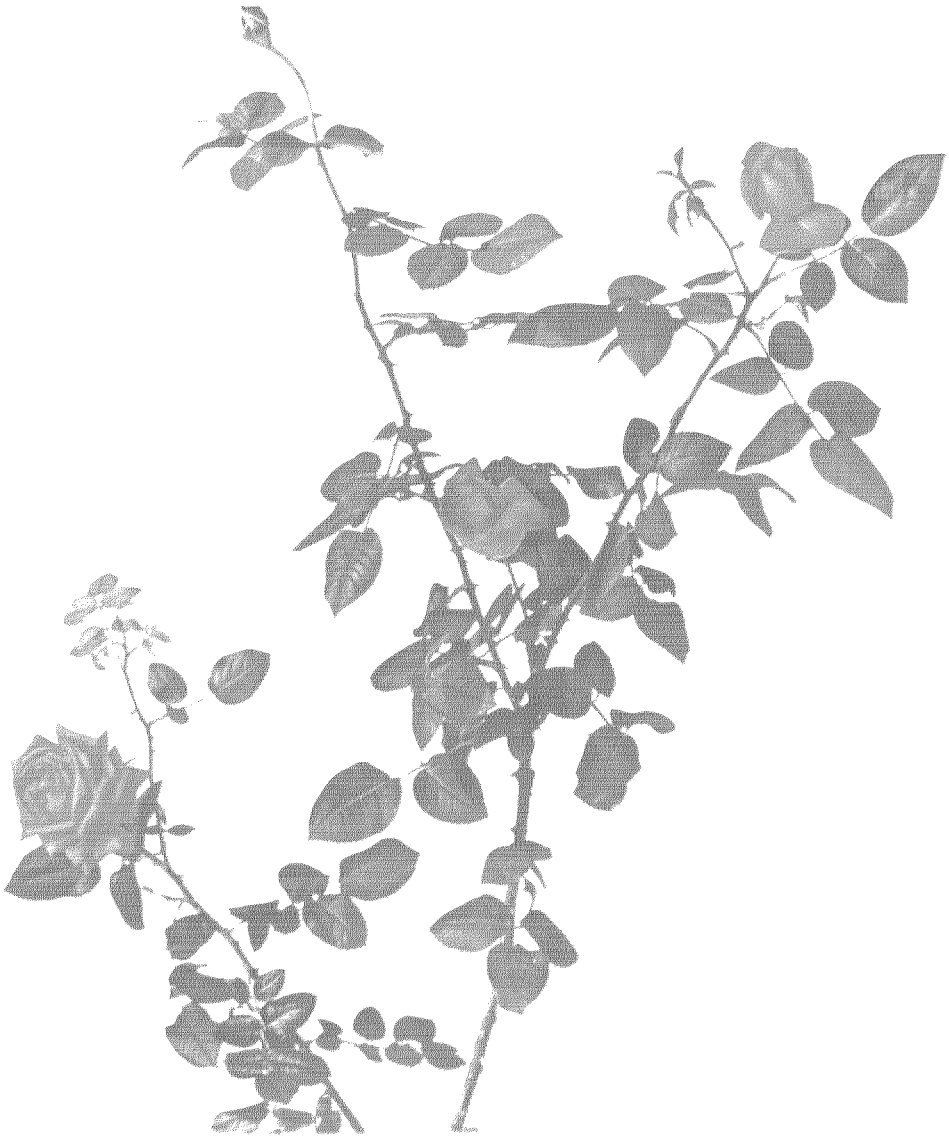
Inventor
H. R. Campbell
By: Robb & Robb
Attorneys Patented May 11, 1954 Plant Pat. 1,274

UNITED STATES PATENT OFFICE 1,274

ROSE PLANT

Harold R. Campbell, Temple City, Calif.

Application April 13, 1953, Serial No. 348,605

1 Claim. (Cl. 47—61)

The present invention relates to a new and distinct variety of rose plant of the hybrid tea class, which was originated by me from seeds planted among a lot of approximately 156 seedlings of miscellaneous known and unknown parentage. This particular variety was derived from one of 8 seeds obtained from a seed pod which I had collected, but on which I failed to note the source or parentage. All of the seeds sprouted, but the present variety was selected therefrom by me as the only one worthy of preservation, and particularly by reason of the fact that it was decidedly different from all of the others of the entire crop. I attribute these differences to a seed mutation, and hence my new variety may be classified as a mutant.

My new variety is especially differentiated from all other varieties of its class by the following unique combination of outstanding characteristics:

(1) The large, full, long-lasting flowers which have up to 200 petals and numerous petaloids during the main growing season, but rarely less than 75 petals in the late fall, this full petalage making a very durable bloom both on the bush and as a cut flower, with the petals usually drying up at the end and remaining intact, instead of falling;

(2) The attractive Bengal Rose color of the flowers, which is quite distinctive for a rose of this class, and which is unusually uniform and holds its color even during hot weather, without bluing;

(3) The strong rose fragrance of the flowers; and (4) The initial waxy ivory color of the thorns, eventually becoming deep mahogany in color on the old wood.

Asexual reproduction of my new variety by budding at Temple City, California, shows that the foregoing characteristics and distinctions come true to form and are established and transmitted through succeeding propagations.

The accompanying drawing shows typical specimens of the blooms, foliage and stems of the new variety in different stages of development.

The following is a detailed description of my new variety, with color terminology in accordance with the Horticultural Color Chart of the British Color Council, except where general color terms of ordinary dictionary significance are obvious:

Type: Hardy; bush; outdoors and greenhouse; seedling; for cut flowers and for garden decoration.

Class: Hybrid tea.

Breeding: Seedling—parentage unknown.

Propagation: Holds its distinguishing characteristics through succeeding propagations by budding.

*Flower*

Locality where grown and observed: Temple City, California.

Flowers borne: Singly; on strong, medium length stems.

Quantity of bloom: Abundant outdoors and in greenhouse; 4-year old bushes have produced as many as 250 or more blooms, and no balling down of blooms when grown near coast.

Continuity: Continuous.

Fragrance: Strong; true rose scent.

Bud:

*Peduncle.*—Medium length; medium caliper; erect. Color—light reddish-green. Prickles—numerous; color—red.

*Before calyx breaks.* — Size — medium. Form—oval; with foliaceous appendages on the surface of the bud; with much-cut foliaceous parts extending beyond the tip of the bud equal to ½ of its length. Color—reddish-green.

*As calyx breaks.*—Color—reddish-green.

*As first petal opens.*—Size—medium to large. Form—ovoid, with definite center point. Color: outside—Bengal Rose, Plate 25; inside—Bengal Rose, Plate 25, with high sheen.

*Opening.*—Opens up well until temperature approaches freezing nightly.

Bloom:

*Size.*—Large; from 5 inches to 6½ inches.

*Petalage.*—Very double; from 75 petals in late fall to 200 in spring and summer; full open blooms show no pollen and are filled in completely with petals and petaloids until late fall when petalage drops and the pollen and stigma become visible; petals arranged regularly in outer rows, but are irregularly arranged at center of flower.

*Form.*—Full; high-centered; petals tightly rolled outward at first and remaining tightly rolled outward at maturity.

Petals:

*Texture.*—Thick; with inside shiny and outside satiny.

*Shape.*—Outside — obovate. Intermediate—obovate. Inside—obovate.

This description of a newly opened flower was made from a rose grown outdoors in the month of November at Temple City, California:

*Color.*—Outside petal: outside surface—Bengal Rose, Plate 25/2 to Plate 25/4, with greater intensity during hot weather; inside surface—Bengal Rose, Plate 25/2 to Plate 25/4; very glossy. Intermediate petal: outside surface—Bengal Rose, Plate 25/2 to Plate 25/4; inside surface—Bengal Rose, Plate 25/2 to Plate 25/4. Inner petal: outside surface—Bengal Rose, Plate 25/2 to Plate 25/4; inside surface—Bengal Rose, Plate 25/2 to Plate 25/4.

This description was made from a rose that was open for three days outdoors in the month of November, at Temple City, California:

*Color.*—Outside petal: outside surface—Bengal Rose, Plate 25/2 to Plate 25/4; inside surface—Bengal Rose, Plate 25/2 to Plate 25/4. Inside petal: outside surface—Bengal Rose, Plate 25/2 to Plate 25/4; inside surface—Bengal Rose, Plate 25/2 to Plate 25/4.

*General color effect.*—Newly opened flower—Bengal Rose, Plate 25/2 to Plate 25/4. Three days open—Bengal Rose, Plate 25/2 to Plate 25/4.

The foregoing colors apply to all petals of the flowers, which, during the mid-summer months of clear and continuous sunshine, almost always have an exceptionally uniform color intensity of Bengal Rose, Plate 25/4, whereas during the winter months in the greenhouse, the color intensity usually is slightly lighter and becomes the shade of Bengal Rose, Plate 25/2.

*Behavior.*—Persist; fading brown; good under all weather conditions.

*Flower longevity.*—On bush in garden—10 days or more in month of November. Cut roses grown outdoors and kept at living-room temperatures—10 days from cutting as buds for cut-flower trade, with sepals just breaking, in month of November. Cut roses grown in greenhouse and kept at living-room temperatures—8 days in November.

*Reproductive organs*

Stamens: Very many; arranged irregularly; mixed with petaloids. Color—yellow.
Filaments: Short; many with anthers. Color—white.
Anthers: Medium size; open at various times. Color—yellow.
Pollen: Abundant. Color—yellow.
Pistils: Many.
Styles: Even; medium length; thin; bunched.
Stigma: Color—red.
Ovaries: All enclosed in calyx.
Hips: None has ever developed.

Sepals: Permanent; long; spear-shaped; recurved. Color—green until dried up and fall.
Seeds: None.

*Plant*

Foliage:

*Leaves.*—Compound of 5 to 7 leaflets; abundant; medium size; moderately leathery.

*Leaflets.*—Shape—ovoid, with acute apex and rounded base. Margin—finely serrated, with thin margin of red color.

*Color.*—Mature: upper surface—normal green; under surface—normal green. Young: upper surface—green to red; under surface—light red.

*Rachis (the supporting stem of the compound leaf).*—Medium. Upper side—grooved; under side—thorny.

*Stipules.*—Medium length; medium width; with medium length points turning out at an angle of less than 90°.

*Disease.*—Resistant to mildew, as determined by comparison with other varieties grown under comparable cultural conditions at Temple City, California; has some mildew at times, but rarely enough to require spraying; no signs of blackspot ever observed.

Growth:

*Habit.*—Bushy; much-branched; attains a normal regrowth of 3 feet to 3½ feet after yearly pruning.

*Growth.*—Free.

*Canes.*—Medium caliper.

*Main stems.*—Color—brown. Thorns—several; medium length; hooked downward; with broad base; color—deep mahogany on old wood. Prickles—few; color—brown. Hairs—none.

*Branches.*—Color—green to brown. Thorns—several; medium length; hooked downward; with broad base. Prickles—few; color—reddish. Hairs—none.

*New shoots.*—Color—Bright red. Thorns—several; medium length; hooked downward; with broad base; color—waxy ivory. Prickles—few; color—reddish. Hairs—none.

I claim:

A new and distinct variety of rose plant of the hybrid tea class, substantially as herein shown and described, characterized particularly as to novelty by its large, full, long-lasting blooms and their unusually numerous petals and petaloids, by the Bengal Rose general color tonality of its blooms and the uniformity of their color and absence of bluing, by the strong rose fragrance of its blooms, and by the unusual initial waxy ivory color of its thorns and their habit of becoming a deep mahogany color as the wood ages.

No references cited.